US00PP36590P2

(12) United States Plant Patent
Maria de Jong

(10) Patent No.: US PP36,590 P2
(45) Date of Patent: Apr. 8, 2025

(54) BARBERRY PLANT NAMED 'JBN 17-002'

(50) Latin Name: *Berberis thunbergii*
Varietal Denomination: JBN 17-002

(71) Applicant: Capstone Plants, Inc., Grand Saline, TX (US)

(72) Inventor: Cornelis Henricus Maria de Jong, Biezenmortel (NL)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 18/665,900

(22) Filed: May 16, 2024

(51) Int. Cl.
*A01H 5/00* (2018.01)
*A01H 6/00* (2018.01)

(52) U.S. Cl.
USPC ..... Plt./241
CPC ..... *A01H 6/00* (2018.05)

(58) Field of Classification Search
USPC ..... Plt./241
CPC ..... A01H 5/00
See application file for complete search history.

(56) References Cited

U.S. PATENT DOCUMENTS

PP18,082 P2 9/2007 Kurowski et al.

*Primary Examiner* — Kent L Bell
(74) *Attorney, Agent, or Firm* — The Webb Law Firm

(57) ABSTRACT

A new and distinct Barberry plant having green/yellow foliage, high branching, and an upright, medium compact growth habit.

3 Drawing Sheets

Botanical classification: *Berberis thunbergii.*
Varietal denomination: 'JBN 17-002'.

BACKGROUND OF THE INVENTION

The present invention comprises a new and distinct variety of Barberry plant having the varietal name 'JBN 17-002'. The new variety was discovered and selected in June of 2016 in Biezenmortel, The Netherlands as the result of a planned breeding program with the purposes of developing *Berberis thunbergii* plants that exhibit yellow foliage with a tight growth habit that do not burn in hot conditions. 'JBN 17-002' is the result of open pollination between *Berberis thunbergii* variety named 'Aurea' (unpatented, female parent) and a group of unpatented *Berberis thunbergia* plants from the breeder's own collection. As such, the exact male parent from this collection is unknown.

The new variety was first asexually reproduced via cuttings in Grand Saline, Texas in September of 2018. The new variety is similar to its female parent in having green/yellow colored leaves, but does not burn in hot conditions and is overall a healthier variety than its female parent. When compared to *Berberis thunbergii* variety named 'Maria' (U.S. Plant Pat. No. 18,082), the varieties are similar in leaf color, but the leaves of 'JBN 17-002' are green/yellow, with the yellow portions brighter in color than 'Maria'. Further, 'JBN 17-002' is less sensitive to powdery mildew and more compact than 'Maria'.

The following traits distinguish 'JBN 17-002' as a new and distinct cultivar from other Barberry varieties known to the breeder:

1. Green/yellow foliage instead of consistent bright yellow foliage throughout;
2. Exhibits more resistance to pests and diseases;
3. Hot climate tolerance; and
4. Upright, with a medium compact growth habit.

DESCRIPTION OF THE DRAWINGS

The accompanying photographic images illustrate the new variety at approximately eight months of age, with the colors being as nearly true as is possible with color illustrations of this type.

DESCRIPTION OF THE PLANT

Figure 1:
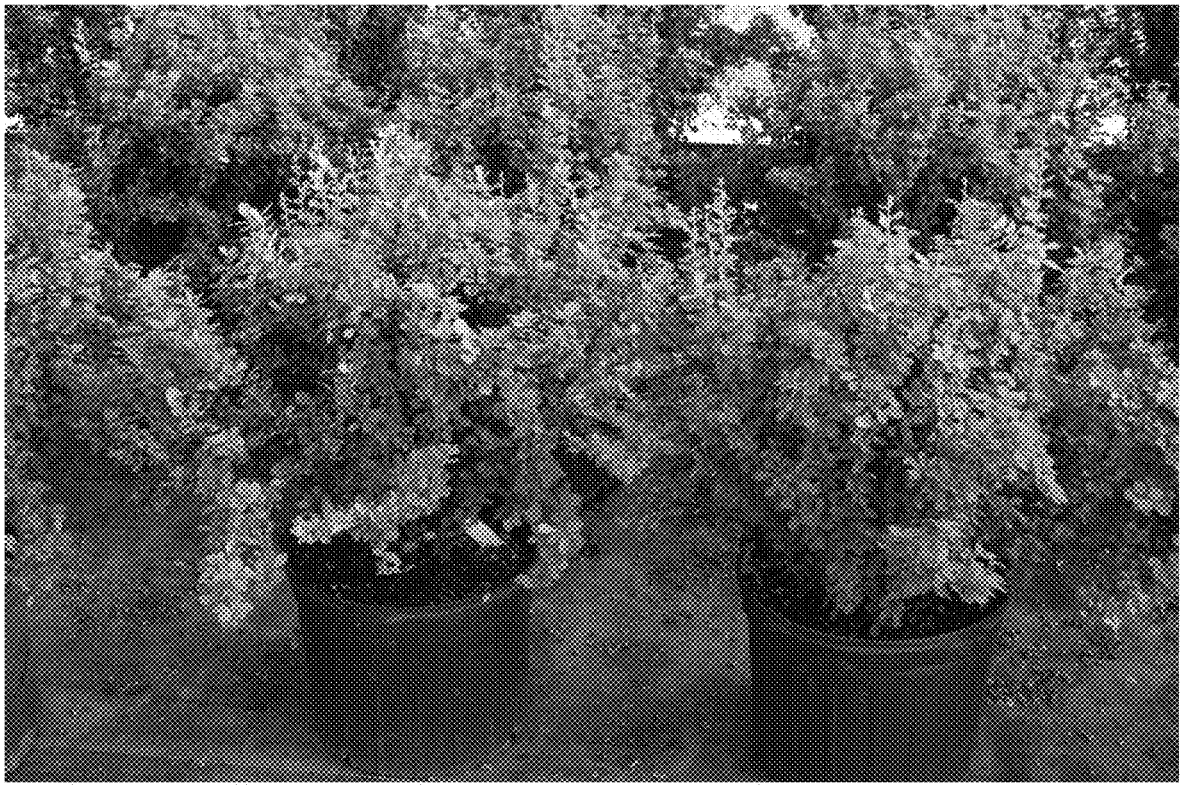
FIG. 1 illustrates multiple plants of the new variety.
Figure 2:
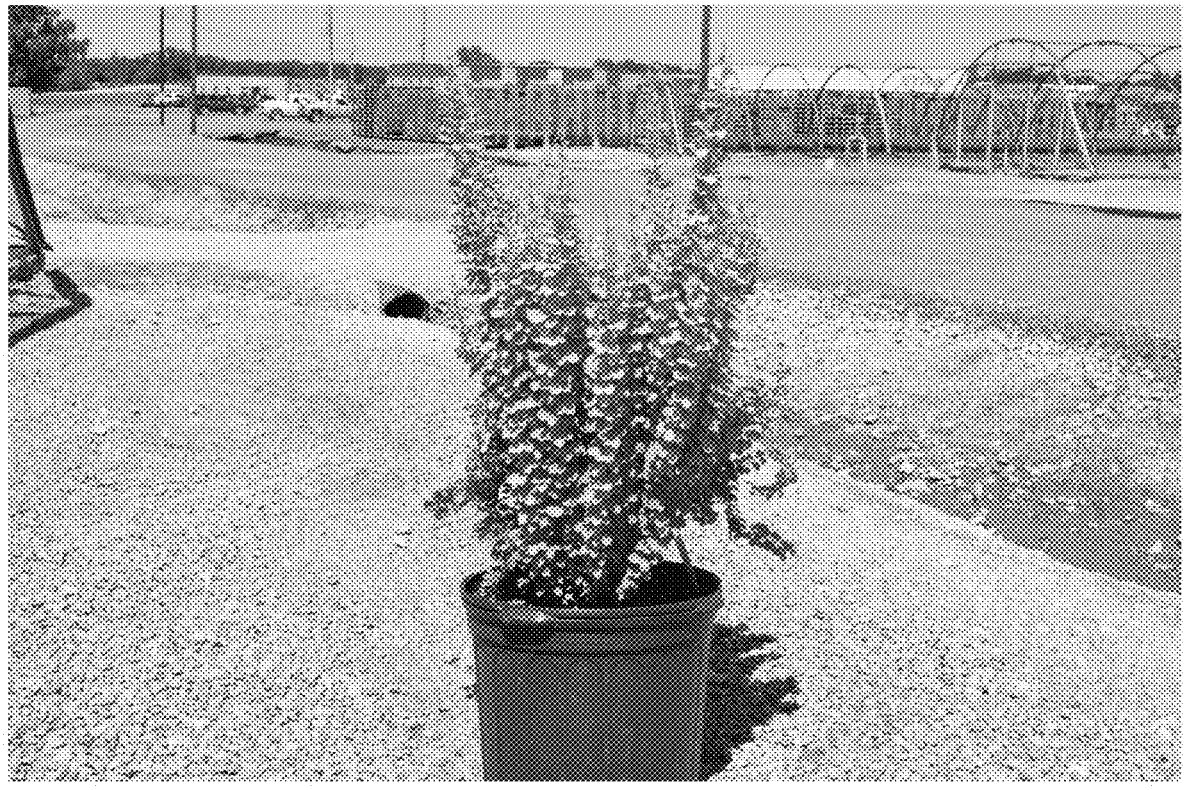
FIG. 2 illustrates an entire plant of the new variety.
Figure 3:
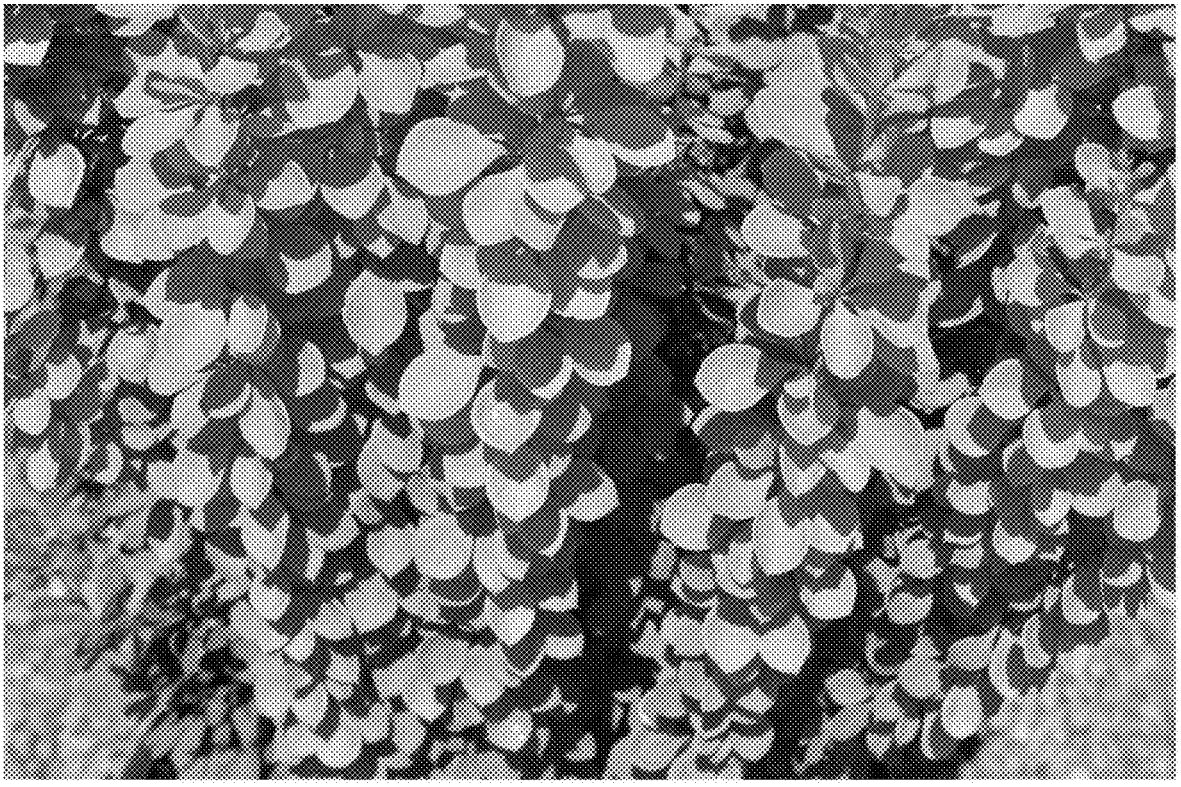
FIG. 3 illustrates a close-up view of the foliage of the new variety.

The following detailed description sets forth the characteristics of the new variety as the result of asexual reproductions performed via cuttings carried out in Grand Saline, Texas. Plants of the new variety were grown outdoors in 20.0 cm (1 gallon/1.8 liter) pots under normal field production conditions until spring arrived, at which time the plants were transferred to an area with at least 30% shade cover. The color readings and measurements were observed indoors under fluorescent lighting near natural lighting from a window on 8 month old plants in Grand Saline, Texas. Color references are primarily to The 1995 R.H.S. Colour Chart of The Royal Horticultural Society of London, Third Edition, except where terms of ordinary significance are used.

PLANT

Time to initiate roots: About 6-8 weeks at an average of 27-35° C.

Time to develop roots: About 18 weeks at an average of 27-35° C.

Heat/cold tolerance: 2023 USDA Hardiness Zone 8b.

Disease/pest resistance: Not susceptible to powdery mildew (*Peronospora viticola*).

Plant:

*Type*.—Deciduous, perennial foliage shrub.

*Habit*.—Upright, medium compact.

*Height*.—Approximately 36.0 cm from top of soil to top of plant.

*Spread*.—Approximately 28.0 cm.

*Vigor*.—Moderate.

*Rooting*.—Fine and fibrous, with RHS 162A coloring.

Branches:

*Number per plant*.—Approximately 56; well-branched, dense, and full.

*Length*.—From 20.0-37.0 cm.

*Width*.—Approximately 2.0 mm.

*Texture*.—Coarse.

*Strength*.—Older growth is firm and newer growth is tender and flexible.

*Internode length*.—From 4.0-6.0 mm.

*Color*.—Immature: RHS 154C. Mature: RHS 177C.

*Spines*.—Number per branch: From 29-36. Shape: Spinose. Length: Approximately 6.0 mm. Width: Approximately 1.0 mm. Color: RHS 199A.

Foliage:

*Arrangement*.—Alternate.

*Size of leaf*.—Length: Approximately 1.8 cm. Width: Approximately 1.6 cm.

*Shape of leaf* (*generally*).—Obovate.

*Shape of apex*.—Obtuse.

*Shape of base*.—Cuneate.

*Texture*.—Upper surface: Very soft and smooth. Lower surface: Soft and smooth, but with a slight texture from venation.

*Margin type*.—Entire.

*Lobing*.—Not really present, more oval-shaped.

*Color*.—Young leaves: Upper surface: RHS 150A. Lower surface: RHS 145C. Mature leaves: Upper surface: RHS 144A. Lower surface: RHS 146C.

*Veins*.—Venation type: Pinnate. Color: Upper surface: RHS 154A. Lower surface: RHS 145B.

*Petiole*.—Length: Approximately 3.0 mm. Diameter: Approximately 1.0 mm. Texture: Smooth. Color: RHS 150A.

Flower description: None observed.

Fruit: None observed.

The invention claimed is:

1. A new and distinct variety of *Berberis thunbergii* plant named 'JBN 17-002', substantially as illustrated and described herein.

* * * * *